(12) United States Patent
Jiang et al.

(10) Patent No.: US 12,331,355 B2
(45) Date of Patent: Jun. 17, 2025

(54) OLIGONUCLEOTIDE CONJUGATE WITH HIGH HYBRIDIZATION PERFORMANCE AND USE THEREOF

(71) Applicant: Daan Gene Co., Ltd., Guangdong (CN)

(72) Inventors: Xiwen Jiang, Guangdong (CN); Ling He, Guangdong (CN); Shilong Lan, Guangdong (CN)

(73) Assignee: Daan Gene Co., Ltd., Guangdong (CN)

( * ) Notice: Subject to any disclaimer, the term of this patent is extended or adjusted under 35 U.S.C. 154(b) by 1305 days.

(21) Appl. No.: 16/957,240

(22) PCT Filed: Apr. 21, 2020

(86) PCT No.: PCT/CN2020/085956
§ 371 (c)(1),
(2) Date: Jun. 23, 2020

(87) PCT Pub. No.: WO2021/189574
PCT Pub. Date: Sep. 30, 2021

(65) Prior Publication Data
US 2022/0333155 A1    Oct. 20, 2022

(30) Foreign Application Priority Data
Mar. 27, 2020 (CN) .......... 202010227318.9

(51) Int. Cl.
*C12Q 1/6876* (2018.01)
*C12Q 1/6851* (2018.01)
*A61K 51/04* (2006.01)

(52) U.S. Cl.
CPC ......... *C12Q 1/6876* (2013.01); *C12Q 1/6851* (2013.01); *A61K 51/0406* (2013.01)

(58) Field of Classification Search
None
See application file for complete search history.

(56) References Cited

FOREIGN PATENT DOCUMENTS

| | | |
|---|---|---|
| CN | 101370817 A | 2/2009 |
| CN | 101978071 A | 2/2011 |
| CN | 106498060 A | 3/2017 |
| CN | 108642145 A | 10/2018 |
| WO | 2013026027 A1 | 2/2013 |

OTHER PUBLICATIONS

Gracie, Interaction of fluorescent dyes with DNA and spermine using fluorescence spectroscopy, Analyst, 139: 3735-3743, 2014. (Year: 2014).*
International Search Report (with English Abstract) issued in PCT/CN2020/085956, mailed Dec. 23, 2020, 9 pages provided.
The extended European search report issued in European application No. 20761131.0, mailed May 27, 2022, 7 pages provided.
Clément Paris et al., "Zip nucleic acids are potent hydrolysis probes for quantitative PCR", Nucleic Acids Research, vol. 38, No. 7, Published online Jan. 13, 2010, 6 pages provided.
Chao-Nan Lin et al., "Comparison of viremia of type II porcine reproductive and respiratory syndrome virus in naturally infected pigs by zip nucleic acid probe-based real-time PCR", BMC Veterinary Research, Sep. 12, 2013, 6 pages provided.
Ehsan Alvandi et al., "Zip nucleic acid: a new reliable method to increase the melting temperature of real-time PCR probes", Journal of Diabetes & Metabolic Disorders, Feb. 4, 2014, 4 pages provided.

* cited by examiner

*Primary Examiner* — Gary Benzion
*Assistant Examiner* — Carolyn L Greene
(74) *Attorney, Agent, or Firm* — HSML P. C.

(57) ABSTRACT

The present invention provides an oligonucleotide conjugate with high hybridization performance and use thereof. The oligonucleotide conjugate of the present invention can be used as a probe for nucleic acid detection, the oligonucleotide conjugate of the present invention can be used to design probes more flexibly, and the conservative regions are more accessible. The specificity of the probe is better, and the fluorescence value of the probe can be significantly improved, the fluorescence background is significantly reduced, and the sensitivity of the probe is greatly improved.

14 Claims, 7 Drawing Sheets
Specification includes a Sequence Listing.

SEQUENCE LISTING

```
<160> NUMBER OF SEQ ID NOS: 15

<210> SEQ ID NO 1
<211> LENGTH: 23
<212> TYPE: DNA
<213> ORGANISM: Artificial sequence
<220> FEATURE:
<223> OTHER INFORMATION: Primer

<400> SEQUENCE: 1
gtagatctcc gtttctattg ctt                                            23

<210> SEQ ID NO 2
<211> LENGTH: 16
<212> TYPE: DNA
<213> ORGANISM: Artificial sequence
<220> FEATURE:
<223> OTHER INFORMATION: Primer

<400> SEQUENCE: 2
cctctagcgc tgcgaa                                                    16

<210> SEQ ID NO 3
<211> LENGTH: 29
<212> TYPE: DNA
<213> ORGANISM: Artificial sequence
<220> FEATURE:
<223> OTHER INFORMATION: Probe

<400> SEQUENCE: 3
tagcactatc aagccttccc tttatacgc                                      29

<210> SEQ ID NO 4
<211> LENGTH: 21
<212> TYPE: DNA
<213> ORGANISM: Artificial sequence
<220> FEATURE:
<223> OTHER INFORMATION: Probe

<400> SEQUENCE: 4
agcactatca agccttccct t                                              21
```

<210> SEQ ID NO 5
<211> LENGTH: 21
<212> TYPE: DNA
<213> ORGANISM: Artificial sequence
<220> FEATURE:
<223> OTHER INFORMATION: Probe

<400> SEQUENCE: 5
tcaagccttc cctttatacg c                                              21

<210> SEQ ID NO 6
<211> LENGTH: 20
<212> TYPE: DNA
<213> ORGANISM: Artificial sequence
<220> FEATURE:
<223> OTHER INFORMATION: Probe

<400> SEQUENCE: 6
agcactatca agccttccct                                                20

<210> SEQ ID NO 7
<211> LENGTH: 20
<212> TYPE: DNA
<213> ORGANISM: Artificial sequence
<220> FEATURE:
<223> OTHER INFORMATION: Probe

<400> SEQUENCE: 7
caagccttcc ctttatacgc                                                20

<210> SEQ ID NO 8
<211> LENGTH: 18
<212> TYPE: DNA
<213> ORGANISM: Artificial sequence
<220> FEATURE:
<223> OTHER INFORMATION: Probe

<400> SEQUENCE: 8
tcaagccttc cctttata                                                  18

<210> SEQ ID NO 9
<211> LENGTH: 18
<212> TYPE: DNA
<213> ORGANISM: Artificial sequence
<220> FEATURE:
<223> OTHER INFORMATION: Probe

<400> SEQUENCE: 9
aagccttccc tttatacg                                                  18

<210> SEQ ID NO 10
<211> LENGTH: 17
<212> TYPE: DNA
<213> ORGANISM: Artificial sequence
<220> FEATURE:
<223> OTHER INFORMATION: Probe

<400> SEQUENCE: 10
cactatcaag ccttccc                                                   17

<210> SEQ ID NO 11
<211> LENGTH: 21
<212> TYPE: DNA
<213> ORGANISM: Artificial sequence
<220> FEATURE:
<223> OTHER INFORMATION: Probe

```
<400> SEQUENCE: 11
agcactatca agccttccct t                                             21

<210> SEQ ID NO 12
<211> LENGTH: 21
<212> TYPE: DNA
<213> ORGANISM: Artificial sequence
<220> FEATURE:
<223> OTHER INFORMATION: Probe

<400> SEQUENCE: 12
tcaagccttc cctttatacg c                                             21

<210> SEQ ID NO 13
<211> LENGTH: 20
<212> TYPE: DNA
<213> ORGANISM: Artificial sequence
<220> FEATURE:
<223> OTHER INFORMATION: Probe

<400> SEQUENCE: 13
agcactatca agccttccct                                               20

<210> SEQ ID NO 14
<211> LENGTH: 20
<212> TYPE: DNA
<213> ORGANISM: Artificial sequence
<220> FEATURE:
<223> OTHER INFORMATION: Probe

<400> SEQUENCE: 14
caagccttcc ctttatacgc                                               20

<210> SEQ ID NO 15
<211> LENGTH: 16
<212> TYPE: DNA
<213> ORGANISM: Artificial sequence
<220> FEATURE:
<223> OTHER INFORMATION: Probe

<400> SEQUENCE: 15
aggccttgag agatat                                                   16
```

OLIGONUCLEOTIDE CONJUGATE WITH HIGH HYBRIDIZATION PERFORMANCE AND USE THEREOF

TECHNICAL FIELD

The present invention belongs to the field of gene detection. In particular, the present invention relates to an oligonucleotide conjugate with high hybridization performance and use thereof.

BACKGROUND

Real-time fluorescence quantitative PCR technology refers to a method of adding fluorescent dyes or fluorescently labeled probes to a PCR reaction system, selecting suitable fluorescent channels on the PCR amplification device, using fluorescence signal accumulation to monitor the entire PCR process in real time, and then performing the quantitative analysis for the unknown template through a standard curve. The commonly used detection methods are dye method and Taqman probe method.

In the dye method, SYBR GREEN, SYBR GREEN and other dyes that can bind to a double-stranded DNA are generally used. When the template in the PCR reaction system is amplified, SYBR GREEN can effectively bind to the newly synthesized double strand. As PCR proceeds, more SYBR GREEN dyes bind to the newly synthesized double strand, and the fluorescent signal detected by the instrument becomes stronger, thereby achieving the purpose of quantification.

The principle of the TaqMan probe method is to add a pair of primers and a specific fluorescently labeled probe to a PCR reaction system. The probe is an oligonucleotide sequence, and a reporter fluorescent group and a quenching group are labeled at both ends of the sequence respectively. The probe is intact and when the two groups are very close, the fluorescent signal emitted by the reporter group is absorbed by the quenching group and does not emit fluorescence. At the beginning of amplification, the double-stranded template dissociates into single strands under denaturing conditions at 95° C. At the annealing temperature, the probe begins to bind to one of the single strands of DNA. During PCR extension, the heat-resistant Taq DNA polymerase degrades the probe with its 5'-3'exonuclease activity to separate the reporter fluorescent group and the quenching fluorescent group, so that the fluorescence monitoring system can receive the fluorescent signal, that is, when a DNA strand is amplified, a fluorescent molecule is formed, which realizes the complete synchronization of the accumulation of fluorescent signals and the formation of PCR products.

In the dye method, during PCR amplification, the dye will be inserted into all double-stranded structures. When non-specific amplification or primer dimer occurs in the experiment, it will greatly affect the accuracy of the results. In addition, the dye method cannot detect multiple target genes in the same reaction tube. The largest difference between the Tagman probe method and the dye method is that the fluorescent signal in the probe method is only derived from the target sequence, so that it will not be affected by non-specific amplification products and primer dimers.

The design of the Taqman probe method utilizes the FRET principle, that is, fluorescence energy resonance transfer. It is an energy transfer phenomenon between two fluorescent molecules in close proximity. When the emission spectrum of the donor fluorescent molecule overlaps with the absorption spectrum of the receptor fluorescent molecule, and the distance between the two molecules is within 10 nm (100 Å), a non-radioactive energy transfer occurs, and the fluorescence of the donor is quenched by the receptor, i.e., FRET phenomenon. When the distance between the donor and the receptor is greater than 100 Å, the effectiveness of FRET between the two fluorescent molecules is reduced or even unable to perform FRET. Therefore, the probe design is limited by the length of the sequence. In order to increase the discrimination of single nucleotide genotyping and provide design flexibility for complex target genes, it is critical to reduce the length of the probe. However, shortening the probe will reduce the melting temperature (TM value), which inhibits the effective binding of the probe to the target sequence at the PCR cycle temperature.

Therefore, those skilled in the art are working to solve the contradiction between the probe design length and the ideal TM value.

SUMMARY OF THE INVENTION

The object of the present invention is to provide a probe and a detection method for nucleic acid detection, especially a probe and a detection method for real-time fluorescence quantitative PCR detection.

In the first aspect of the present invention, an oligonucleotide conjugate is provided, the structure of the oligonucleotide conjugate is shown in the following Formula I:

$$R\text{-}N\text{-}Q\text{-}D, \qquad\qquad I$$

wherein R is an optional fluorescent group, N is an oligonucleotide unit, Q is a quenching group, and D is a cationic unit.

In another preferred embodiment, R is none or a fluorescent group.

In another preferred embodiment, in Formula I, each "-" is independently a chemical bond or linker.

In another preferred embodiment, in Formula I, each "-" is independently a phosphodiester bond.

In another preferred embodiment, the oligonucleotide conjugate is a PCR detection probe or primer.

In another preferred embodiment, N is an oligonucleotide sequence of 3-60 bases; preferably an oligonucleotide sequence of 8-40 bases; more preferably an oligonucleotide sequence of 10-30 bases.

In another preferred embodiment, in Formula I, the 5' end of N is connected to R, and the 3' end of N is connected to Q.

In another preferred embodiment, in Formula I, the 3' end of N is connected to R, and the 5' end of N is connected to Q.

In another preferred embodiment, R is selected from the group consisting of FAM, VIC, HEX, NED, ROX, TET, JOE, TAMRA, CY3, and CY5.

In another preferred embodiment, Q is selected from the group consisting of Eclipse, BHQ-1, BHQ-2, and BHQ-3.

In another preferred embodiment, the cationic unit D contains one or more amino groups.

In another preferred embodiment, D is an organic cation unit of a mer, wherein a is an integer between 1 and 30; preferably, a is an integer between 2 and 20; more preferably, a is an integer between 3 and 10.

In another preferred embodiment, the organic cation is spermine.

In the second aspect of the present invention, use of the oligonucleotide conjugate according to the first aspect of the present invention for preparing a primer or probe for PCR detection is provided.

In the third aspect of the present invention, a kit comprising the oligonucleotide conjugate according to the first aspect of the present invention is provided.

In another preferred embodiment, the kit includes a probe made from the oligonucleotide conjugate according to the first aspect of the present invention, or includes a primer made from the oligonucleotide conjugate according to the first aspect of the present invention.

In another preferred embodiment, the kit further includes one or more reagents selected from the group consisting of:
  a PCR buffer, dNTPs, hot start Taq enzyme, reverse transcriptase, and RNase inhibitor.

In the fourth aspect of the present invention, a PCR reaction system is provided, which comprises the oligonucleotide conjugate according to the first aspect of the present invention.

In another preferred embodiment, the reaction system is a real-time fluorescence quantitative PCR reaction system.

In another preferred embodiment, the PCR reaction system includes a probe made from the oligonucleotide conjugate according to the first aspect of the present invention, or includes a primer made from the oligonucleotide conjugate according to the first aspect of the present invention.

In another preferred embodiment, the PCR reaction system includes a target nucleic acid, and an oligonucleotide conjugate according to the first aspect of the present invention, wherein the oligonucleotide unit N in the oligonucleotide conjugate is at least reversely complementary (matched or completely matched) to a portion of the sequence of the target nucleic acid.

In another preferred embodiment, the PCR reaction system further includes one or more reagents selected from the group consisting of:
  PCR buffer, dNTPs, hot start Taq enzyme, reverse transcriptase, and RNase inhibitors.

In the fifth aspect of the present invention, a method for real-time fluorescence quantitative PCR is provided, and the method includes the steps of:
  (1) providing a nucleic acid sample of a subject to be tested;
  (2) preparing a PCR reaction system for the PCR detection:
  wherein the PCR reaction system includes: the nucleic acid sample provided in step (1), and the oligonucleotide conjugate according to the first aspect of the present invention. Wherein the oligonucleotide conjugate is present in the PCR reaction system in the form of a probe and/or primer.

It should be understood that, within the scope of the present invention, the technical features specifically described above and below (such as the Examples) can be combined with each other, thereby constituting a new or preferred technical solution which needs not be described one by one herein.

DETAILED DESCRIPTION OF INVENTION

Figure 1:
FIG. 1 shows an exemplary structure of the oligonucleotide conjugate of the present invention that includes an oligonucleotide sequence of SEQ ID NO.: 15.

The present inventor has obtained an oligonucleotide conjugate through extensive and intensive research. The oligonucleotide conjugate of the present invention can be used as a PCR probe to make the probe design more flexible and the conserved regions more available. The experimental results show that the specificity of the probe is better, and the fluorescence value of the probe is significantly higher, the fluorescence background is significantly reduced, and the sensitivity of the probe is greatly improved.

Before describing the present invention, it should be understood that the present invention is not limited to the specific methods and experimental conditions as described, because such methods and conditions may vary. It should also be understood that the terminology used herein is for the purpose of describing specific embodiments only and is not intended to be limiting, and the scope of the present invention will be limited only by the appended claims.

Unless otherwise defined, all technical and scientific terms used herein have the same meaning as commonly understood by those of ordinary skill in the art to which this invention belongs. As used herein, when referring to specifically recited values, the term "about" means that the value may vary from the recited value by no more than 1%. For example, as used herein, the expression "about 100" includes 99 and 101, and all values between 99 and 101 (e.g., 99.1, 99.2, 99.3, 99.4, etc.).

Although any method and material similar or equivalent to those described in the present invention can be used in the practice or testing of the present invention, the preferred methods and materials are exemplified herein.

Oligonucleotide Conjugate

The object of the present invention is to provide a novel oligonucleotide conjugate, the oligonucleotide sequence of which is partially coupled with a cationic unit that can reduce electrostatic repulsion between it and the target gene. The cationic unit contains a certain number of cationic monomers, which can adjust the charge of the entire oligonucleotide conjugate and improve the stability for the binding of the oligonucleotide conjugate to the target sequence.

The oligonucleotide conjugate of the present invention has the structure shown in the following Formula I.

wherein R is an optional fluorescent group, N is an oligonucleotide unit, Q is a quenching group, and D is a cationic unit.

In general, it is customary in the art to place a quenching group on the outermost end of the oligonucleotide conjugate (e.g., the outermost end of the 3' end). The present inventor has unexpectedly discovered that in an oligonucleotide conjugate containing a cationic unit, coupling the cationic unit to the outside of the quenching group can significantly improve the stability and specificity for the binding of the oligonucleotide conjugate to the target sequence. Specifically, when the oligonucleotide conjugate is used as a PCR probe, the specificity of the probe is better, the probe fluorescence value is significantly higher, the fluorescence background is significantly reduced, and the probe sensitivity is greatly improved.

In a preferred embodiment of the present invention, the cationic unit is organic cationic units of polymers (organic cationic polymers).

The organic cation is referable spermine:

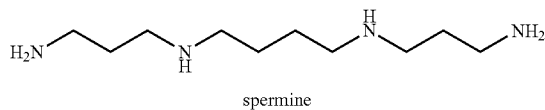 [SMILES: NCCCNCCCCNCCCN]

spermine

Therefore, in a preferred embodiment of the present invention, the cationic unit is polyspermine. For the preparation method of polyspermine, please refer to the existing conventional methods in the art for the preparation. For example, a phosphoramidite-modified spermine monomer can be subjected to a coupling reaction to obtain a polyspermine connected with a phosphorite bond (phosphodiester bond). The synthesis reaction can be carried out on an automated DNA synthesizer. The structure of Spermine Phosphoramidite is as follows:

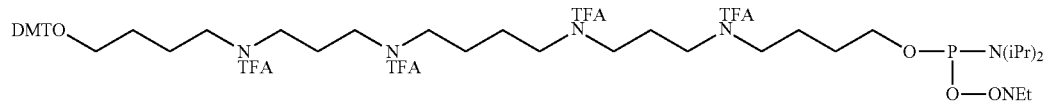

In a preferred embodiment of the present invention, the cationic unit is an organic cation unit of a mer, wherein a is an integer between 1 and 30; preferably, a is an integer between 2 and 20; more preferably, a is an integer between 3 and 10; preferably, the structure of the cationic unit is as follows:

—[P⁻O₃—(CH₂)₄—N⁺H₂—(CH₂)₃—N⁺H₂—(CH₂)₄—N⁺H₂—(CH₂)₃—N⁺H₂—(CH₂)₄—O]$_{a-1}$—P⁻O₃—(CH₂)₄—N⁺H₂—(CH₂)₃—N⁺H₂—(CH₂)₄—N⁺H₂—(CH₂)₃—N⁺H₂—(CH₂)₄—OH

When the oligonucleotide conjugate is used as a probe, it can flexibly increase the TM value of the probe (5-15° C.), which can make the design of the probe shorter, the background of the probe lower, and the sensitivity higher, while the conservative region designed is more available, and it also has its own unique advantages in terms of amplification efficiency and SNP typing; the oligonucleotide conjugate of the present invention can also be used as a modified primer to increase the TM value of the primer while greatly increasing the amplification efficiency of the primer.

Based on the oligonucleotide conjugate of the present invention, the present invention provides a probe technology for real-time fluorescence PCR. The length of the probe sequence of the present invention is designed according to the purpose of the experiment. The probe consists of a base sequence that matches the target nucleic acid, a fluorescent reporter group modified at the 5' end, and a fluorescence quenching group and a polycation unit sequentially coupled at the 3' end (preferably a polyamino derivative).

The synthesis of the oligonucleotide conjugate of the present invention can be carried out using conventional methods in the art.

The synthetic route of the oligonucleotide conjugate of the present invention is summarized as follows:

The first step is deblocking. Trichloroacetic acid (TCA) was used to remove DMT on the nucleoside attached to the synthesis column carrier to expose the 5' hydroxyl group for further condensation.

The second step is coupling. The base monomer is mixed with tetrazole to form a phosphoramidite tetrazole active intermediate and enters into the synthesis column. It undergoes a nucleophilic reaction with the 5' hydroxyl group of the nucleoside attached to the support of the synthesis column, the synthesized oligonucleotide chain extends one base.

The third step is capping. To prevent the unreacted 5' hydroxyl group in the previous step from being extended in the subsequent synthesis cycle, the hydroxyl group is blocked with an acetylation reagent.

The fourth step is oxidation. The nucleotides that complete the coupling reaction are connected by a phosphorite bond (trivalent phosphorus), and the trivalent phosphorus is oxidized to pentavalent phosphorus with a solution of iodine in tetrahydrofuran. The above synthesis steps is cycled, the synthesis is completed when the oligonucleotide chain extends to the required length.

When synthesizing the dye labeling group or polycationic unit, the monomers in the second step can be replaced with dye monomers or polycationic monomers (such as spermine), respectively.

As used herein, "matching" or "pairing" of bases means that the corresponding bases in the two nucleotide sequences form a reverse complementary double-strand structure according to the principle of pairing of A and T, and G and C.

As used herein, "matching" in the present invention means that the sequences are completely complementary between the primer or probe and the template, or not completely complementary, but with only an appropriate base mismatch (such as 1, 2, or 3 base mismatches).

As used herein, "complete matching" in the present invention means that the sequences are completely complementary without any base mismatch between the primer or probe and the template.

As used herein, the term "nucleic acid" or "oligonucleotide" specifically refers to a polymer that includes ribonucleic acids and/or deoxyribonucleic acids especially covalently bonded via phosphodiester bonds between subunits (in some cases phosphorothioate, methylphosphonate, etc.). The term covers naturally occurring nucleic acids as well as synthetic nucleic acids.

As used herein, the term "probe" is an oligonucleotide sequence that matches the target sequence, usually paired with the sequence between the upstream primer and the downstream primer of the target sequence, the 5' end of the probe is generally connected to a fluorescent group, and the 3' end thereof is connected to a quenching group. When the complete probe is paired with the target sequence, the fluorescence emitted by the fluorophore is quenched due to proximity of the 3' end quencher, but during the extension reaction, the 5' exonuclease activity of the polymerase cleaves the probe to separate the fluorophore from the quencher. As the number of amplification cycles increases, the released fluorophores are continued to be accumulated, so that the fluorescence intensity is directly proportional to the number of amplification products, presenting an S-shaped curve.

In the present invention, the 3' end of the primer is usually modified or blocked. Typically, the 3' end of hydroxyl group of the primer is modified and blocked in a way with a fluorophore or a quenching group (blocking group).

The 5' end or the 3' end of the fluorescent primer may be labeled with a fluorophore. Correspondingly, the 3' end or 5' end of the fluorescent primer may be labeled with a quenching group, the fluorophore or quenching group labeled at the 3' end of the fluorescent primer blocks the —OH (hydroxyl group) at the 3' end, so that is cannot be extended in normal PCR amplification reactions.

Representative examples of fluorophores include (but not limited to): FAM, Cy5, Texas Red, HEX, VIC, TET, JOE, TAMRA, ROX, LC Red610, LC Red640, LCCyan500, Yakima Yellow, or a combination thereof.

Representative examples of quenching groups include (but not limited to): BHQ1, BHQ2, BHQ3, Eclipse, TAMRA, Dabcyl, or a combination thereof.

In the present invention, the type of modified nucleotide is not particularly limited, and may be: A, T, C, G or a combination thereof.

In the present invention, a single fluorescent primer or multiple fluorescent primers can be used in an optimized reaction system.

Real-Time Fluorescence Quantitative PCR

Real-time fluorescence quantitative PCR technology is a leap in DNA quantitative technology. Using this technology, quantitative and qualitative analysis can be performed on DNA and RNA samples. Quantitative analysis includes absolute quantitative analysis and relative quantitative analysis. At present, real-time fluorescence PCR technology has been widely used in basic scientific research, clinical diagnosis, disease research and drug research and development and other fields.

Use of the Present Invention

The present invention can be widely used for diagnostic and non-diagnostic detection, and can be used for detection of point mutation (drug resistance), single nucleotide polymorphism, insertion and deletion mutation.

In another preferred embodiment, the detection of the present invention may be the detection of foods and pathogenic microorganisms (bacteria, viruses, etc.).

In a preferred embodiment, the present invention is used to detect whether there is a mutation at a mutation site of a gene to be tested (disease-related genes, drug metabolism, drug therapy-related genes, etc.).

In addition, the present invention can be widely used in human genetic diseases, longevity and aging related genes, health risk related genes, disease susceptibility genes, tumor personalized treatment related SNP, pathogen resistance detection.

The term "nucleic acid sample" is used broadly herein and is intended to include various sources and compositions containing nucleic acids. Exemplary biological samples include, but are not limited to: cell samples, environmental samples, samples obtained from the body, especially body fluid samples, and human, animal, or plant tissue samples. Non-limiting examples include, but are not limited to: cells, whole blood, blood products, erythrocyte, leukocyte, buffy coat, plasma, serum, swabs, urine, sputum, saliva, semen, lymph, amniotic fluid, cerebrospinal fluid, peritoneal effusion, pleural effusion, biopsy sample, cyst fluid, synovia, vitreous humor, aqueous humor, bursa, eye wash, eye aspiration fluid, plasma, serum, broncho alveolar lavage, lung aspirate, animal (especially human) or plant tissues, including but not limited to liver, spleen, kidney, lung, intestine, brain, heart, muscle, pancreas, cell culture and lysates, extracts or materials and parts obtained from the above samples. Preferably, the sample is derived from a biological sample of human, animal or plant. The sample may be selected from the group consisting of cells, tissues, tumor cells and body fluids, such as blood, blood products such as buffy coat, plasma and serum, urine, body fluids, sputum, feces, CSF and sperm, epithelial swabs, biopsies, bone marrow samples and tissue samples, preferably organ tissue samples. The term "sample" also includes processed samples, such as preserved, fixed and/or stabilized samples. However, the nucleic acid-containing sample may also be a crude sample containing nucleic acids in a released form, and may be provided by the lysate obtained from the corresponding biological sample.

The main advantages of the present invention are:
1. The probe design is more flexible, and the conserved region is more accessible;
2. Better specificity of the probe;
3. The TM value of probe can be adjusted;
4. the amplification efficiency can be improved;
5. the non-specific amplification can be reduced and false positive results can be avoided;
6. The fluorescence value of probe is significantly higher, the fluorescence background is significantly reduced, and the probe sensitivity has been greatly improved;
7. The better stability of the probe.

The present invention will be further described in detail below in conjunction with specific embodiments. It should be understood that these examples are only used to illustrate the present invention and not to limit the scope of the present invention. The experimental methods without detailed conditions in the following examples are generally in accordance with the conventional conditions such as those described in Sambrook. J et al. "Molecular Cloning: A Laboratory Manual" (translated by Huang Peitang et al., Beijing: Science Press, 2002), or in accordance with the conditions recommended by the manufacturer. Unless otherwise stated, percentages and parts are calculated by weight. Unless otherwise specified, the experimental materials and reagents used in the following examples can be obtained from commercially available channels.

Example 1. Preparation of Oligonucleotides and Conjugates Thereof

ZNA probe ((Zip nucleic acid) was synthesized using solid-phase phosphoramidite triester method, the monomer reagents used for synthesis were all phosphoramidite monomer in structure. The amino, hydroxyl, and phosphorous acid groups on each monomer had protective groups, which were deprotected with concentrated ammonia after synthesis. On the solid phase support, the synthesis of the oligonucleotide chain was completed from the 3' end to the 5' by the DNA synthesizer, and adjacent nucleotides were connected by 3'5' phosphodiester bonds. The synthesis of the ZNA probe was conducted with each base on the DNA synthesizer through a four-step chemical reaction.

The first step was deblocking. Trichloroacetic acid (TCA) was used to remove the DMT on the nucleoside attached to the support of the synthesis column to expose the 5'hydroxyl group for the next condensation.

The second step was coupling. The base monomer was mixed with tetrazole to form a phosphoramidite tetrazole active intermediate which entered the synthesis column. It underwent a nucleophilic reaction with the 5'hydroxyl group of the nucleoside attached to the support of the synthesis column, and the synthetic oligonucleotide chain extended one base.

The third step was capping. To prevent the unreacted 5'hydroxyl group in the previous step from being extended in the subsequent synthesis cycle, the hydroxyl group was blocked with an acetylating reagent.

The fourth step was oxidation. The nucleotides for the coupling reaction were connected by a phosphorous acid bond (trivalent phosphorus), and the trivalent phosphorus was oxidized to pentavalent phosphorus with a solution of iodine in tetrahydrofuran. The above synthesis steps were cycled, the synthesis was completed when the oligonucleotide chain extended to the required length.

When synthesizing the dye labeling group or polycationic unit, the monomers in the second step could be replaced with dye monomers or polycationic monomers (such as spermine), respectively.

Operation on Synthesizer

The synthesis on 3900 DNA synthesizer (ABI, USA) was driven by the inert gas, argon. The argon was used as an inert gas and had a specific gravity greater than air, which could be used as a protective gas for synthesis reagents and participated in the synthesis drive.

Some synthesis raw materials were listed as follows:

| name | Cat. No | manufacturers |
| --- | --- | --- |
| 6-FAM fluorescein monomer | 10-5901-90, 100 umole/bottle | Glen research |
| spermine monomer | 10-1939-90, 100 umol/bottle | Glen research |
| BHQ1 monomer | 10-5941-90, 100 umol/bottle | Glen research |
| ECLIPSE monomer | 10-5925-90, 100 umol/bottle | Glen research |
| dA | 10-1000-20, 2 g/bottle | Glen research |
| dG | 10-1029-20, 2 g/bottle | Glen research |
| dT | 10-1030-20, 2 g/bottle | Glen research |
| dC | 10-1015-20, 2 g/bottle | Glen research |

Operation process for ZNA probe synthesis was as follows:
1) Checking the environmental temperature and humidity, preparing the reagents and supports as needed, and balanced at room temperature; checking the argon pressure value, the total pressure gauge is 35 Mpa, and the partial pressure gauge is 0.4-0.5 Mpa;
2) Introducing the ZNA probe sequence into the synthesizer and setting up the synthesis program, including the volume of all reagents, the times of pumping liquid, coupling time;
3) Flushing the base and modification lines with 15 ml of anhydrous acetonitrile;
4) Preparing anhydrous acetonitrile, syringe, needle and pipette. According to the molecular weight and mass of the base monomer and the modified monomer, aspirating anhydrous acetonitrile with a syringe to dissolve to 0.05 mol/L, shaking and mixing it well.
5) Adding auxiliary reagents (Deblock, Activator, CAPA/B, Oxidizer) and anhydrous acetonitrile to the synthesizer; installing the dissolved monomer reagents at the corresponding positions of the synthesizer; inserting the synthetic column support into the inner warehouse BANK according to the introduction order of the synthetic sequence;
6) Performing prime, pumping liquid to check whether the pipeline is unimpeded, executing Purge, and checking whether the pressure of the synthetic instrument panel is normal;
7) Running the synthesis software and executing the synthesis program.

The reaction parameters of each cycle were as follows:
1. Washing with acetonitrile, 200 ul for 3 times, aspirating the liquid;
2. Deprotection using trichloroacetic acid, 180 ul for 3 times, aspirating the liquid;
3. Washing with acetonitrile, 200 ul for 3 times, aspirating the liquid;
4. Mixed injection of tetrazole and base with injection volumes of 45 ul and 30 ul respectively, and a reaction time of 60s; aspirating the liquid;
5. Mixed injection of acetic anhydride and 1-methylimidazole with an injection volume of 30 ul, and aspirating the liquid;
6. Washing with acetonitrile, 200 ul for 3 times, aspirating the liquid;
7. Tetrahydrofuran in iodine, 60 ul, aspirating the liquid;
8. Washing with acetonitrile, 200 ul for 3 times, aspirating the liquid;
9. Repeating 8;
10. Drying the synthesis column.

Note: When synthesizing the dye and polycation, the dye monomer and cationic monomer were used to replace the "base" in step 4, respectively.

Post-Synthesis Treatment

The synthesized ZNA probe was cleaved from the synthesis column support with concentrated ammonia, and at the same time, the protecting groups of the monomers, modifying groups, fluorescent dyes and the like in the sequence were removed. Ammonia cleavage refers to the cleavage of the ester bond on the synthesis column support at the 3' end of the probe sequence. The specific steps were as follows:
1) Taking several cryogenic vials and numbering them according to the probe name;
2) Taking the synthesis column with ZNA probes out of the inner chamber of the synthesizer;
3) Using a syringe needle to poke the CPG in the synthesis column into the cryogenic vials in step 1);
4) Adding 800 ul of fresh concentrated ammonia to each cryogenic vial and covering the tube tightly;
5) Setting the temperature of the water bath to 28° C., and removing the cryogenic vials after 6 hours of reaction;
6) Preparing a 2.5 ml absorbent cotton syringe and wetting it with sterile purified water;
7) Preparing a 5 ml centrifuge tube, transferring the ZNA probe after the aminolysis to an absorbent cotton syringe, filtering off CPG, and flowing the probe into the 5 ml centrifuge tube;
8) After equilibrating the NAP-25 column with sterilized purified water for 5 times, transferring the ZNA probe into the NAP-25 column with a pipette. After flowing the sample into the column filler by gravity, adding sterile purified water to elute the target sample. Using a 5 ml centrifuge tube to collect the components that flew out first (color layering) to remove ammonia and free fluorescent dye.

9) After equilibrating the NAP-25 column with sterilized purified water for 10 times, putting it in the refrigerator at 4° C., ready for use.

Example 2. Test for the Probe Effect

The sequences of the primer and probe for *Chlamydia trachomatis* (CT) were designed from GENEBANK. These primer and probe were used in PCR reaction enzyme system containing heat-resistant DNA polymerase, high-quality deoxyribonucleoside triphosphates (dNTPs), and PCR reaction solutions containing $Mg^{2+}$ and other components. The test was performed by in vitro nucleic acid cyclic amplification through the fluorescence PCR instrument.

TABLE 1

CT primer

| primer | 5'-3' sequence | SEQ ID NO.: | Tm value |
|---|---|---|---|
| Forward | GTAGATCTCCGT TTCTATTGCTT | 1 | 52.7 |
| Reverse | CCTCTAGCGCTGCGAA | 2 | 53 |

TABLE 2

CT long probe (29mer-DNA)

| primer/ probe | 5'-3' sequence | SEQ ID NO.: | Tm value | label |
|---|---|---|---|---|
| 29mer-DNA | TAGCACTATCAAGCC TTCCCTTTATACGC | 3 | 64.3 | 5'FAM, 3'BHQ1 |

TABLE 3 common Taqman short probe

| primer/ probe | 5'-3' sequence | SEQ ID NO.: | Tm value | label |
|---|---|---|---|---|
| 21mer01-DNA | AGCACTAT CAAGCCTT CCCTT | 4 | 55.9 | 5'FAM, 3'BHQ1 |
| 21mer02-DNA | TCAAGCCT TCCCTTTA TACGC | 5 | 57.2 | 5'FAM, 3'BHQ1 |
| 20mer03-DNA | AGCACTAT CAAGCCTT CCCT | 6 | 54.4 | 5'FAM, 3'BHQ1 |
| 20mer04-DNA | CAAGCCTT CCCTTTAT ACGC | 7 | 55.4 | 5'FAM, 3'BHQ1 |

TABLE 4

MGB probe

| primer/ probe | 5'-3' sequence | SEQ ID NO.: | Tm value | label |
|---|---|---|---|---|
| 18mer01-MGB | TCAAGCCTTC CCTTTATA | 8 | 71 | 5'FAM, 3'MGB |
| 18mer02-MGB | AAGCCTTCCC TTTATACG | 9 | 69 | 5'FAM, 3'MGB |
| 17mer01-MGB | CACTATCAAG CCTTCCC | 10 | 71 | 5'FAM, 3'MGB |

TABLE 5

ZNA probe

| primer/ probe | 5'-3' sequence | SEQ ID NO.: | Tm value | label |
|---|---|---|---|---|
| 21mer01-ZNA | AGCACTATCAA GCCTTCCCTT | 11 | 66 | 5'FAM, 3'BHQ1 + ZIP |
| 21mer02-ZNA | TCAAGCCTTCC CTTTATACGC | 12 | 67.3 | 5'FAM, 3'BHQ1 + ZIP |
| 20mer01-ZNA | AGCACTATCAA GCCTTCCCT | 13 | 65.1 | 5'FAM, 3BHQ1 + ZIP |
| 20mer02-ZNA | CAAGCCTTCCC TTTATACGC | 14 | 66.1 | 5'FAM, 3BHQ1 + ZIP |

Wherein the 5' end of the common probe was modified with the FAM fluorescent reporter group, and the 3' end thereof was modified with the BHQ1 fluorescent quenching group;

The 5' end of the ZNA probe and the control ZNA probe was modified with the FAM fluorescent reporter group, and the 3' end thereof was modified with the ZIP (cationic unit polyspermine) and BHQ1 fluorescence quenching groups. The ZIP can be designed to contain 1, 2, 3, 4, and 5 spermine monomers according to experimental needs.

Wherein the specific upstream and downstream primers and probes were specific primer and probe sequences complementary to the target sequence of the target gene.

Above sequences of primer and probe were synthesized according to the method in Example 1.

PCR Reaction 1. 45 ul of the ready-made reaction system: 40 ul of reaction solution A, 3 ul of reaction solution B, 2 ul of CT positive quantitative reference.

Wherein the reaction solution A was a mixture of primer and probe buffer; the reaction solution B was Taq enzyme system.

2. PCR Reaction Conditions

Denaturation at 93° C. for 2 min; 10 cycles of 93° C. for 45 s, 55° C. for 1 min; then 30 cycles of 93° C. for 30 s, 55° C. for 45 s; and fluorescence collection and detection at 55° C.

2.1 Comparison of the Effects of Two ZNA Probes

The amplification effects of the ZNA probe (ZNA probe, method ①) of the present invention and the control ZNA probe (method ②) were compared.

The ZNA probe of the present invention was 21mer02-Z5 (i.e., 21mer02-ZNA, its 3' end was sequentially modified with BHQ1 fluorescence quenching group and ZIP (5 polyspermine)), and the control ZNA probe was 21mer02-5Z (its 3' end was sequentially modified with ZIP (5 polyspermine) and BHQ1 fluorescence quenching group).

Figure 2:
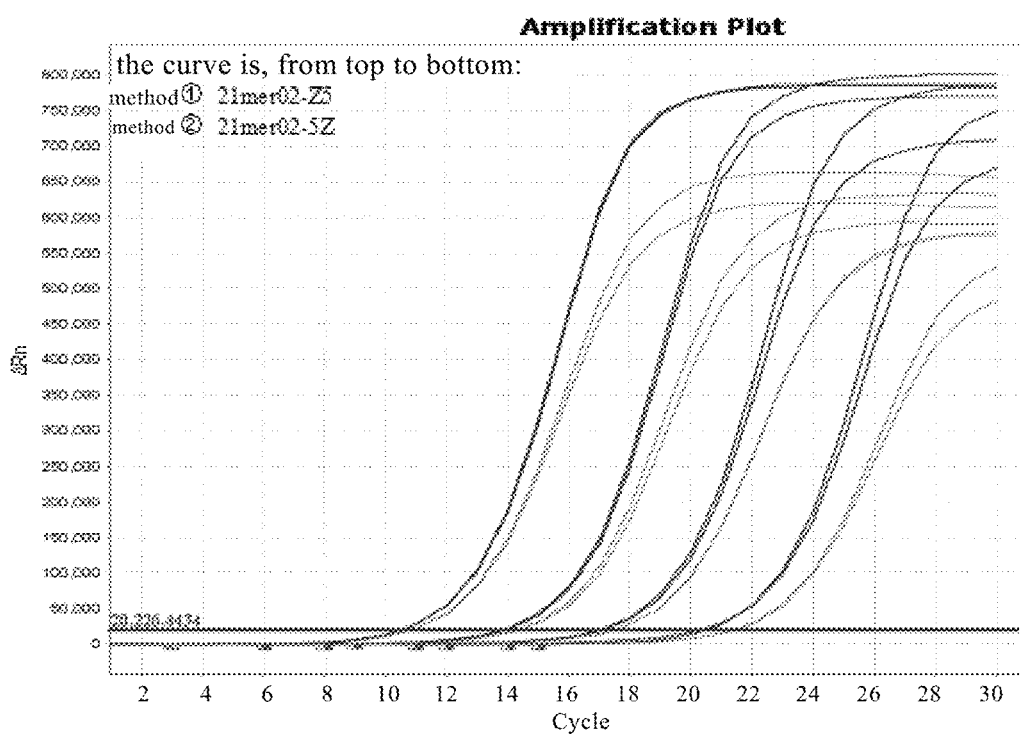
FIG. 2 shows the fluorescence value of two ZNA probes labeled with 5 ZIP units, having the same base sequence.

As shown in FIG. 2, when two ZNA probes labeled with 5 ZIP units (5 polyspermine) with the same base sequence were used to detect gradient diluted plasmids, but the fluorescence value of the ZNA probe was about 35% higher than that of the control ZNA probe, and the Ct value was lower (Δ Ct≈0.5). Additionally, the lower the template concentration, the smaller the Ct value of the ZNA probe of the present invention than that of the control ZNA probe. Δ Ct=0.95 at a gradient concentration of $1\times10^4$.

Figure 3:
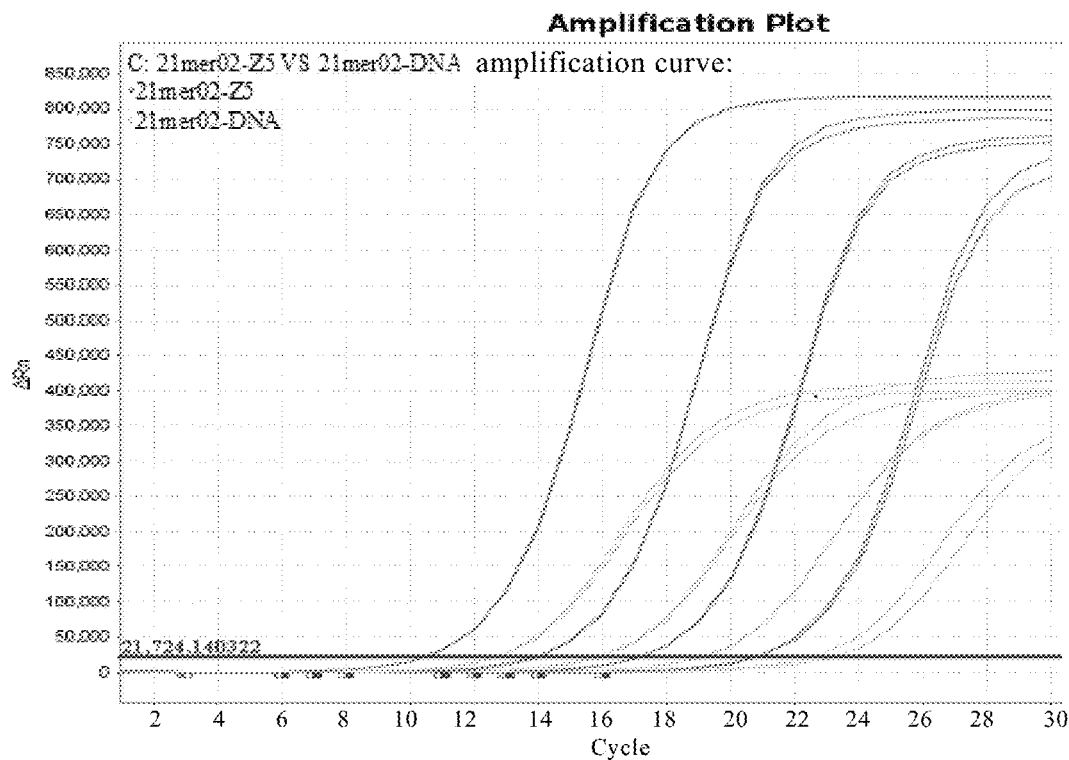
FIG. 3 shows the results of comparison of a ZNA probe coupled with 5 ZIP units with a common Taqman probe of the same base sequence.

As shown in FIG. 3, the ZNA probe coupled with 5 ZIP units was compared with the common Taqman probe with the same base sequence. The fluorescence value of the ZNA probe is 2.05 times higher than that of the common probe with the same sequence, and at the same time, the Ct value was significantly reduced, A Ct=2.12, and the sensitivity was increased by 6.4 times.

2.2 Number of Coupled ZIP Units

Figure 4:
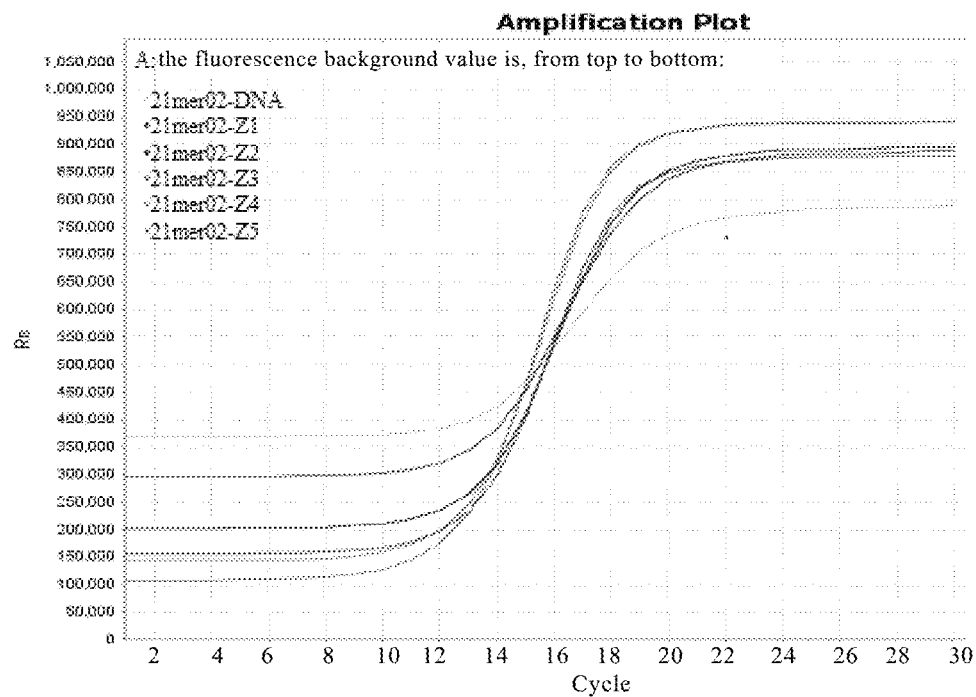
FIG. 4 shows that as the number of ZIP couplings increases, the fluorescence background value of the ZNA probe shows a gradual downward trend.
Figure 5:
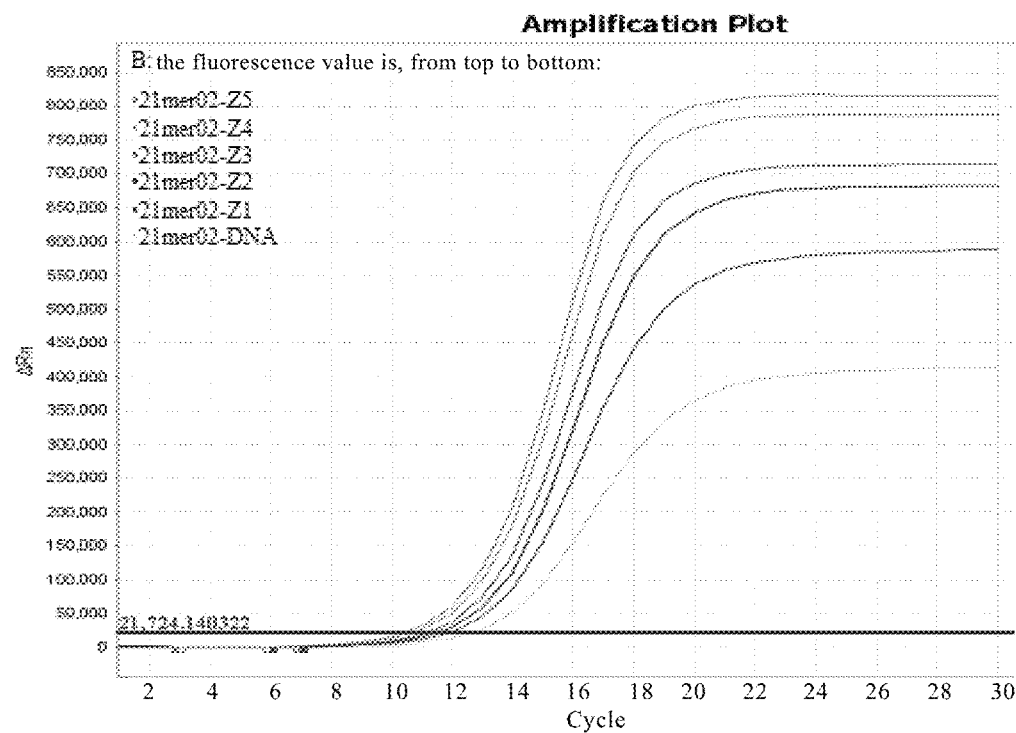
FIG. 5 shows that as the number of ZIP coupling increases, the Ct value in the ZNA probe shows a decreasing trend.

One of the advantages of the ZNA probe is that researchers can flexibly add the number of ZIP units according to the sequence length and the Tm value that needs to be improved. As shown in FIG. 4, as the number of ZIP coupling increased (from 1 to 5 monomer couplings), the fluorescence background value of the synthesized ZNA probe showed a gradual downward trend; and the amplification curve at the exponential phase was better, showing that the fluorescence value for each cycle increased more and was closer to the ideal exponential amplification curve. At the same time, as shown in FIG. 5, as the number of ZIP coupling increased, the Ct value in the ZNA probe showed a decreasing trend, $Ct_{Z5}-Ct_{Z1}=|-1.34|$ 2.3 Quenching Group BHQ1 and ECLIPSE are two commonly used non-luminescent dyes. The two groups have different absorption wavelength ranges. When comparing the synthesis modes, the effects of BHQ1 and ECLIPSE on the two synthesis modes should be considered.

Figure 6:
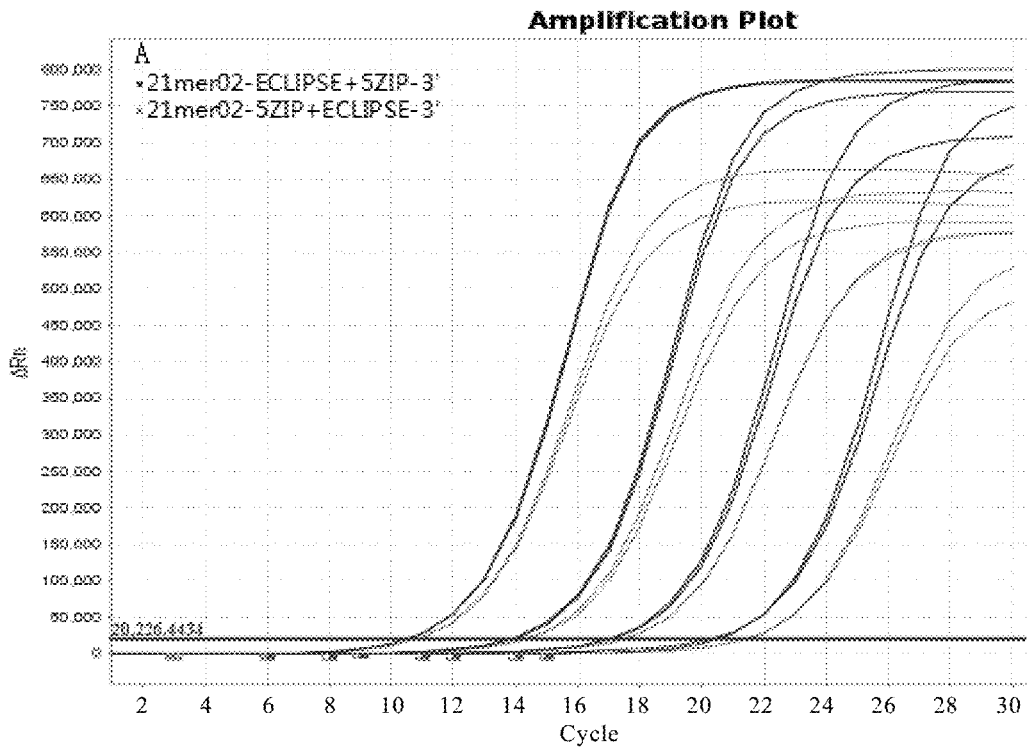
FIGS. 6 and 7 show the amplification effect of the probe when the quenching group is coupled to different positions.
Figure 7:
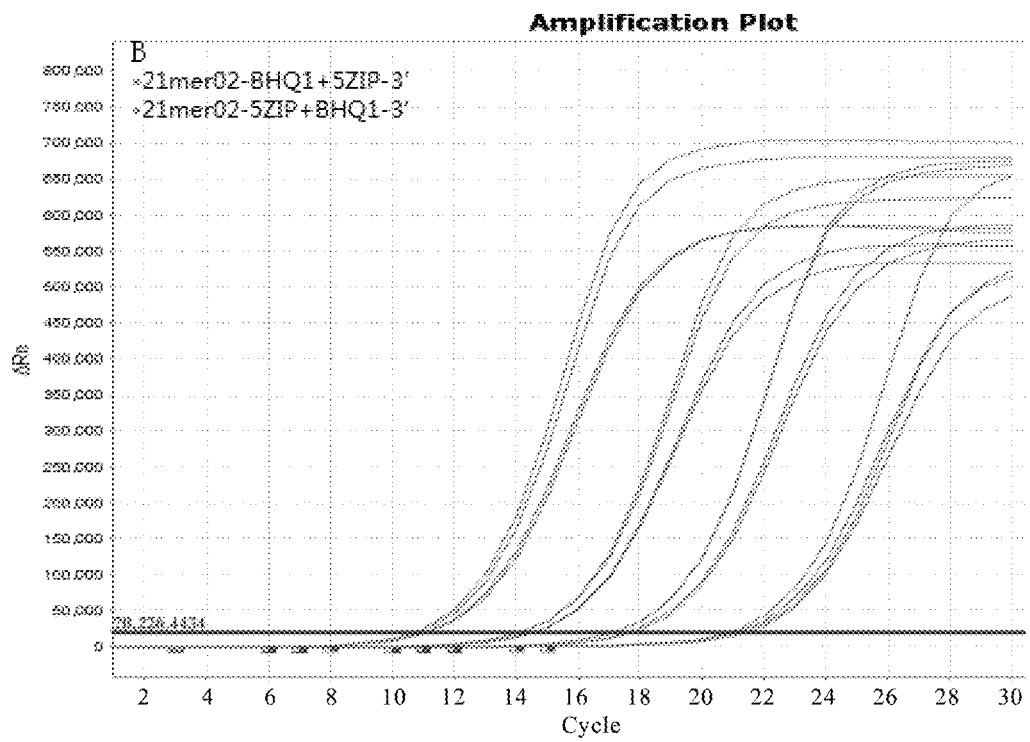
Figure 8:
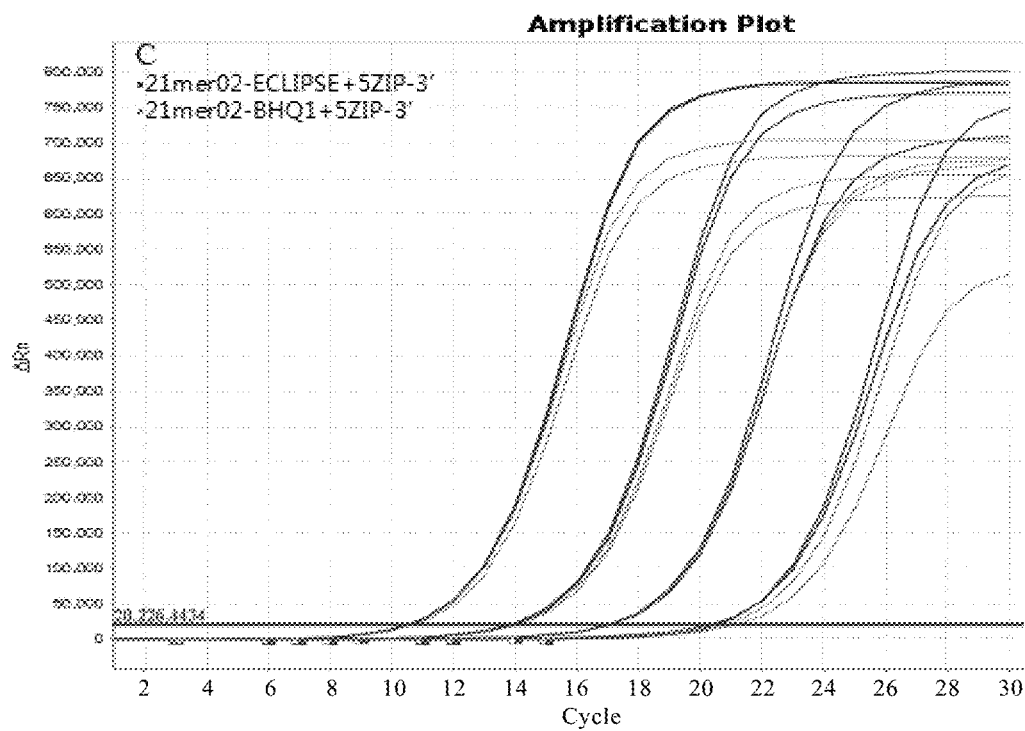
FIGS. 8 and 9 show the amplification effect of the probe when different quenching groups are coupled to the same position.
Figure 9:
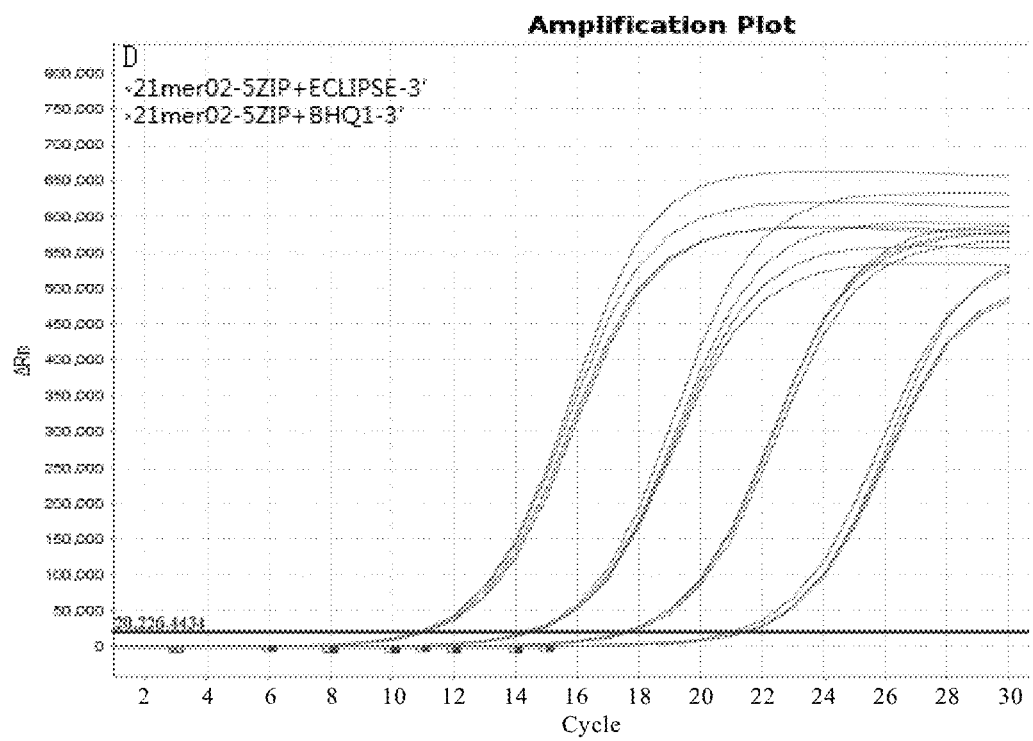

As shown in FIG. 6 and FIG. 7, when $10^7$-$10^2$ gradient diluted plasmids were detected, when ECLIPSE and BHQ1 are adjacent to the base and ZIP, its PCR amplification efficiency was superior to that with both dyes labeled at the 3' end of the sequence. The fluorescence value was increased by 20-30%, and the Ct value was lower (A Ct 0.5); as shown in FIGS. 8 and 9, when ECLIPSE and BHQ1 were adjacent to the base and ZIP, there was no difference in the performance of the two dyes in Ct value; when the two dyes were simultaneously labeled at the 3' end of the sequence, there was no difference in Ct value. This showed that there was no effect of the two commonly used quenching groups on different coupling positions.

Example 3. Common Taqman, MGB, ZNA Probe Sequences are Preferred

Three types of short probes were designed on the basis of CT long probes (29mer-DNA, theoretical Tm value of 64.3° C.) with three to four probes designed for each, their PCR amplification curves were compared, and one was selected for each group to compare PCR amplification performance. 20mer03-DNA was selected from four common Taqman short probes (theoretical Tm value of 54.4-57.2° C., there was no obvious difference in PCR amplification efficiency), ready for use; for three MGB probes, with a sequence length of 17-18 bases and a theoretical Tm value of 69-71° C., the amplification efficiency of 17mer01-MGB was better than that of the other two probes, with a 20-30% higher fluorescence value and a 0.5-0.8 lower Ct value; for four ZNA probes, with a sequence length of 20-21 and a theoretical Tm value of 65.1-67.3° C., there was no significant difference in the Ct values of the four probes, and 21mer02-ZNA was selected for use.

The amplification curve evaluation, plasmid sample evaluation, detection specificity, clinical sample evaluation and comparison of MGB probe and ZNA probe sequence differences after extending or shortening were mainly performed on the four groups of probes.

Figure 10:
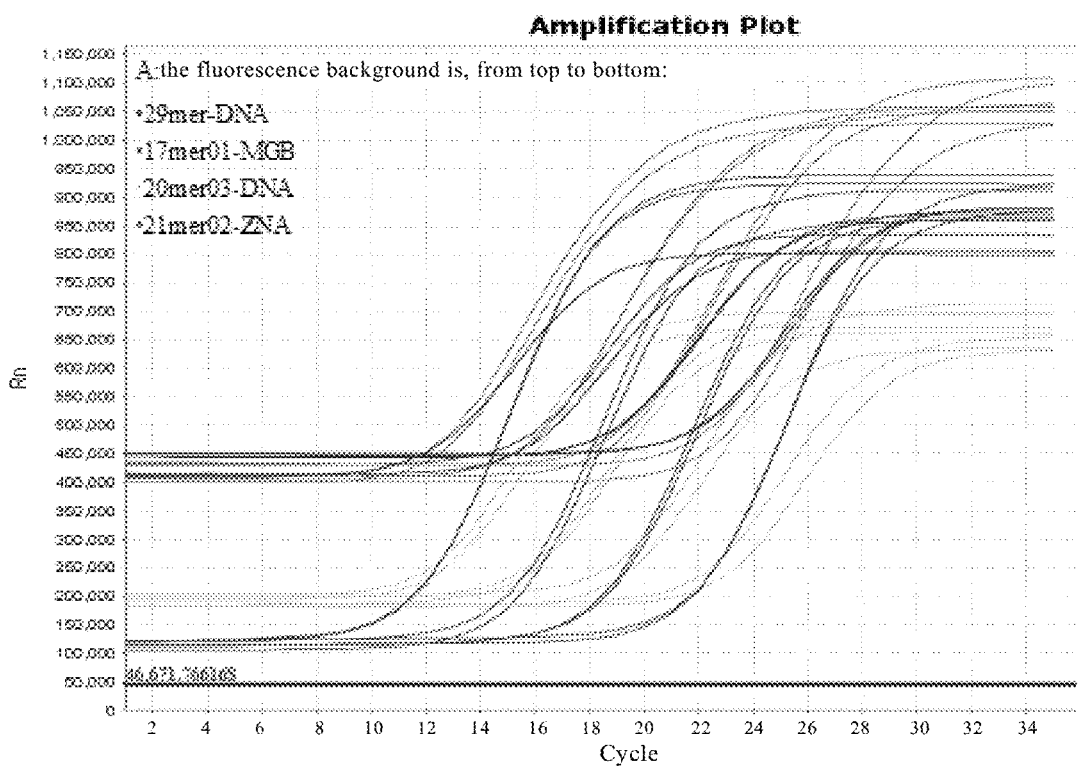
FIG. 10 shows a comparison of the fluorescence background values of different probes.

3.1 Comparison of Amplification Curves 3.1.1 Comparison of Fluorescence Background Values As shown in FIG. 10, the fluorescence background values of the four groups of probes showed that the 21mer02-ZNA probe had the lowest fluorescence background value, followed by the 20mer03-DNA probe; the background of the 17mer01-MGB probe was equivalent to that of the 29mer-DNA probe.

The fluorescence background is related to the PCR amplification sensitivity. The sequence of the ZNA probe had the same length as the common short probe. The preferred 20mer03-DNA probe had the lowest fluorescence background among the four Taqman short probes. The results of this experiment showed that the fluorescence background value of the 21mer02-ZNA probe was 41% lower than that of the 20mer03-DNA probe, and 73% and 75% lower than that of the 17mer01-MGB probe and 29mer-DNA probe, respectively.

3.1.2 Comparison of Amplification Efficiency

Figure 11:
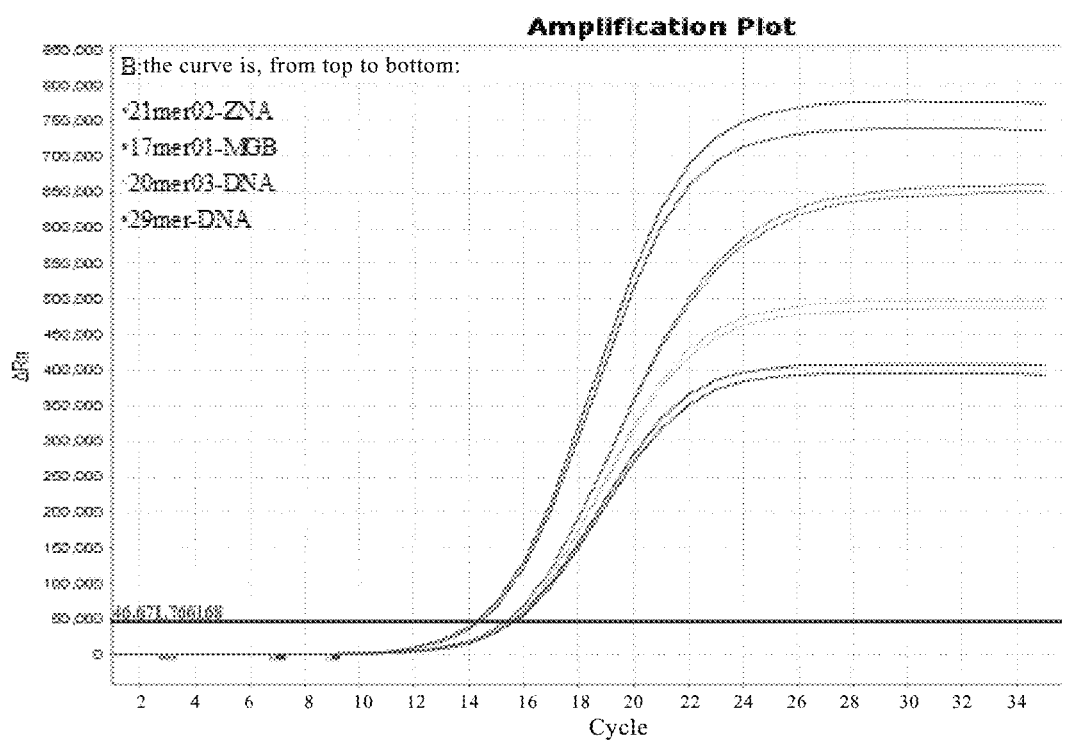
FIG. 11 shows a comparison of the amplification efficiency of different probes.

As shown in FIG. 11, the 21mer02-ZNA probe was superior to other types of probes: the fluorescence value was 90% higher than the 29mer-DNA probe, 52% higher than the 20mer03-DNA probe, and 17% higher than the 17mer01-MGB probe; the Ct values were 1.4, 1.3 and 1.1 earlier, respectively.

3.2 Results of Plasmid Samples Evaluation

For the aforementioned 4 groups of probes, gradient dilutions of plasmids ($10^7$-$10^4$ copies/μl) were used as standards for 10 repeated detections, and the standard curve was calculated. The results showed that the Ct values of the four groups of probes had a good linear relationship with the template concentration. The correlation coefficients $R^2$ of the four groups of probes were: 21mer02-ZNA 0.998, 17mer01-MGB 0.997, 20mer03-DNA 0.998, 29mer-DNA 0.996.

3.3 Specific Test Results

Using sterilized and purified water as a template, the PCR system prepared by the aforementioned four groups of probes was repeatedly tested for 48 times, and a positive reference of a low concentration (10') was made for each group. The results showed that each system could obtain good detection specificity, and no non-specific amplification occurred.

3.4 Test for Probe Freeze-Thaw

The four groups of probes underwent freeze-thaw for 0 times, 5 times, 10 times, 15 times, and 20 times respectively to test the stability of the four groups of probes after repeated freeze-thaw cycles.

Figure 12:
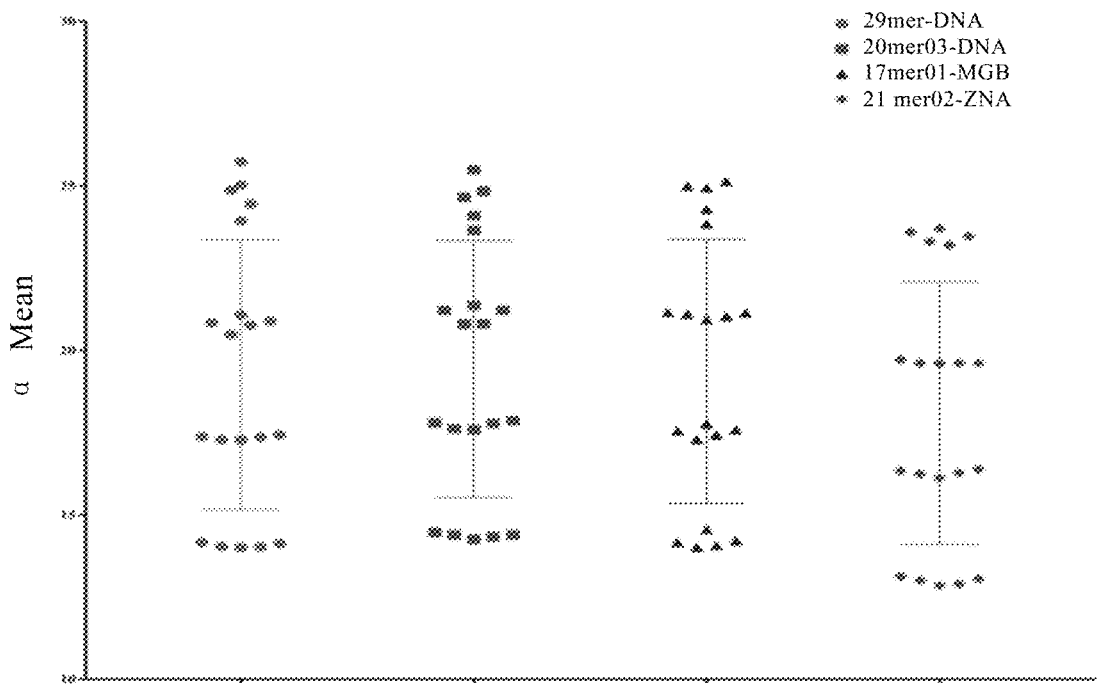
FIG. 12 shows the stability detection results of different probes after repeated freeze-thaw.

The results showed that the ZNA probe had the best detection stability after multiple freeze-thaw cycles. The coefficient of variation (CV %) of the Ct value at different concentration templates was 0.5-1.4, and the average Ct value was lower than other probes (FIG. 12); The Ct value of the lowest concentration ($10^4$ copies/μl) deviated the least (CV %=1.4), which was significantly better than the other three groups of probes (29mer-DNA 3.7%, 20mer03-DNA 1.7%, 17mer01-MGB 2.2%).

3.5 Results of Clinical Samples Evaluation

Figure 13:
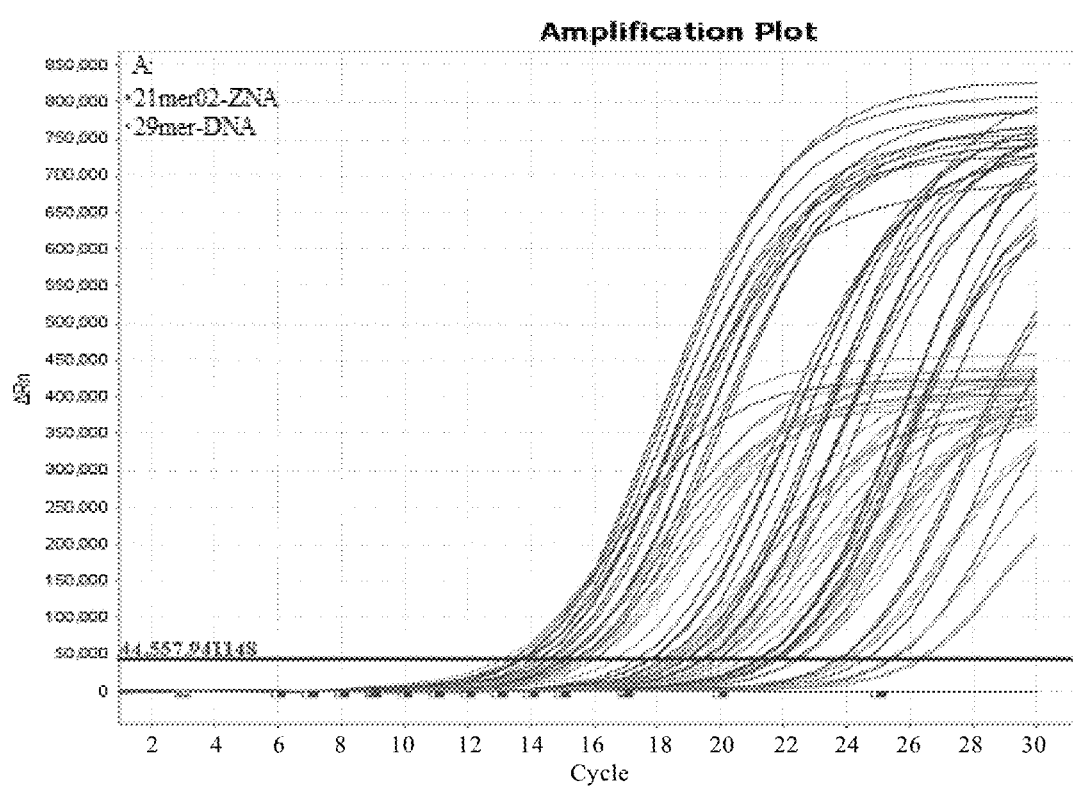
FIG. 13 shows the detection results of clinical samples.

As shown in FIG. 13, 35 clinical samples were tested with the aforementioned four groups of probes. The 21mer02-ZNA probe was significantly better than the 29mer-DNA common Taqman probe. The Ct value of the curve was earlier and the fluorescence value was higher.

A sample of high-concentration samples was selected for gradient dilution, diluted to 200, 150, 100 and 50 copies/μl, respectively and the aforementioned four groups of probes were used for detection. The results were shown in Table 6. The sensitivity of the ZNA probe was best. With 90% positive as the indicator, it could be found that when the sample concentration was 200, 150 and 100 copies/μl, the detection rate of the ZNA probe corresponded to 100%, 95% and 90%, respectively, which is higher than the other three labeled probes. Especially at the lowest concentration of 50 copies/μl, the detection rates of the four groups of probes all decreased, but the detection rate of the ZNA probe was still highest with a relatively slow downward trend.

TABLE 6

| | concentration (copies/μl) | | | |
|---|---|---|---|---|
| | 200 | 150 | 100 | 50 |
| 29mer-DNA | 20/20 | 14/20 | 12/20 | 5/20 |
| 20mer03-DNA | 16/20 | 17/20 | 12/20 | 5/20 |
| 17mer01-MGB | 15/20 | 14/20 | 12/20 | 6/20 |
| 21mer02-ZNA | 20/20 | 19/20 | 18/20 | 14/20 |
| sample size | 20 | | | |

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

In accordance with 37 CFR 1.821(c)(1), the content of the Sequence Listing, entitled "Sequence Listing" and filed herewith, is incorporated by reference herein. The ASCII text file of the Sequence Listing was generated on Jan. 23, 2025 and has a size of 3000 bytes.

The invention claimed is:

1. An oligonucleotide conjugate, wherein the structure of the oligonucleotide conjugate is shown in the following Formula I:

R—N-Q-D,     I wherein R is an optional fluorescent group, N is an oligonucleotide unit, Q is a quenching group, and D is a cationic unit.

2. The oligonucleotide conjugate of claim 1, wherein N is an oligonucleotide sequence of 3-60 bases.

3. The oligonucleotide conjugate of claim 2, wherein N is an oligonucleotide sequence of 8-40 bases.

4. The oligonucleotide conjugate of claim 1, wherein the cationic unit D contains one or more amino groups.

5. The oligonucleotide conjugate of claim 1, wherein D is an organic cationic unit of a mer, wherein a is an integer between 1 and 30.

6. The oligonucleotide conjugate of claim 5, wherein the organic cationic unit is spermine.

7. The oligonucleotide conjugate of claim 5, wherein a is an integer between 2 and 20.

8. The oligonucleotide conjugate of claim 7, wherein a is an integer between 3 and 10.

9. The oligonucleotide conjugate of claim 1, wherein in Formula I, the 5' end of N is connected R, and the 3' end of N is connected to Q.

10. The oligonucleotide conjugate of claim 1, wherein in Formula I, the 3' end of N is connected to R, and the 5' end of N is connected to Q.

11. A kit comprising the oligonucleotide conjugate of claim 1.

12. A PCR reaction system, comprising the oligonucleotide conjugate of claim 1.

13. The PCR reaction system of claim 12, wherein the PCR reaction system includes a probe made from the oligonucleotide conjugate of claim 1.

14. A method for real-time fluorescence quantitative PCR, wherein the method comprises the steps of:
(1) providing a nucleic acid sample of a subject to be tested;
(2) preparing a PCR reaction system and performing PCR detection:
wherein the PCR reaction system comprises: the nucleic acid sample provided in step (1), and the oligonucleotide conjugate of claim 1.

* * * * *